United States Patent [19]

Wicks et al.

[11] Patent Number: 5,294,729

[45] Date of Patent: Mar. 15, 1994

[54] PROCESS FOR THE PREPARATION OF A BLOCK OLIGOCARBONATE

[75] Inventors: Douglas A. Wicks, Mt. Lebanon, Pa.; Dittmar K. Nerger, Krefeld, Fed. Rep. of Germany; Rick L. Archey, Pleasant Hills, Pa.; Gary W. Munko, Coraopolis, Pa.

[73] Assignee: Miles Inc., Pittsburgh, Pa.

[21] Appl. No.: 97,743

[22] Filed: Jul. 27, 1993

Related U.S. Application Data

[63] Continuation of Ser. No. 965,128, Oct. 22, 1992, abandoned, which is a continuation-in-part of Ser. No. 802,677, Dec. 4, 1991, abandoned.

[51] Int. Cl.$^5$ ............................ C07C 69/96; C07C 68/06
[52] U.S. Cl. ................................. 558/268; 528/371
[58] Field of Search ............................................. 558/268

[56] References Cited

U.S. PATENT DOCUMENTS

| | | | |
|---|---|---|---|
| 3,998,908 | 12/1976 | Buxbaum | 260/860 |
| 4,216,298 | 8/1980 | Schreckenberg et al. | 525/439 |
| 4,267,303 | 5/1981 | Konig et al. | 528/171 |
| 4,281,101 | 7/1981 | Schreckenberg et al. | 528/196 |
| 4,598,129 | 7/1986 | Borman et al. | 525/439 |
| 4,927,903 | 5/1990 | Schreckenberg et al. | 528/176 |

FOREIGN PATENT DOCUMENTS

| | | |
|---|---|---|
| 0216106 | 8/1985 | European Pat. Off. |
| 1420232 | 2/1969 | Fed. Rep. of Germany. |
| 2636784 | 2/1978 | Fed. Rep. of Germany. |
| 2919629 | 11/1980 | Fed. Rep. of Germany. |
| 898775 | 6/1962 | United Kingdom. |
| 954500 | 4/1964 | United Kingdom. |
| 1139412 | 1/1969 | United Kingdom. |
| 1567517 | 5/1980 | United Kingdom. |

OTHER PUBLICATIONS

"Polymer Engineering and Science", Mar. 1982/vol. 22, No. 4, pp. 229-233.

Primary Examiner—Mary C. Lee
Assistant Examiner—Michael G. Ambrose
Attorney, Agent, or Firm—Joseph C. Gil; Aron Preis

[57] ABSTRACT

A process for preparing a block oligocarbonate is disclosed. The oligocarbonate conforms to

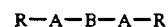

or

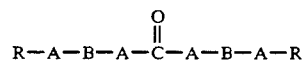

where R denotes hydrogen or

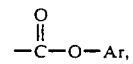

and where A denotes an aromatic carbonate structure conforming to

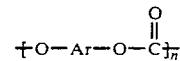

where Ar is an aromatic radical, n is 2-6 and where B is the residue of an aliphatic polyol is disclosed. In the process a high molecular weight aromatic polycarbonate is reacted, in the melt and in the presence of a catalyst, with an aliphatic polyol. The block oligocarbonate is useful as a reactant in a process for the preparation of copolymers.

12 Claims, No Drawings

PROCESS FOR THE PREPARATION OF A BLOCK OLIGOCARBONATE

This application is a continuation of Ser. No. 965,128, which was filed on Oct. 22, 1992 now abandoned, which in turn is a continuation-in-part Ser. No. 07/802,677 filed on Dec. 4, 1991, now abandoned.

FIELD OF THE INVENTION

The invention relates to thermoplastic molding compositions, in particular to molding resins which contain copolycarbonates and to a process for their manufacture.

SUMMARY OF THE INVENTION

A process for preparing a block oligocarbonate is disclosed. The oligocarbonate conforms to

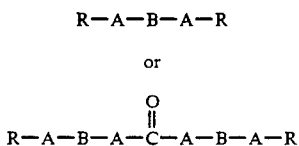

where R denotes hydrogen

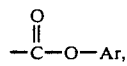

and where A denotes an aromatic carbonate structure conforming to

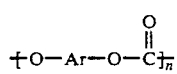

where Ar is an aromatic radical, n is 2-6 and where B is the residue of an aliphatic polyol, with the proviso that said B is bonded to said A through the terminal carboxyl in said A. According to the process an aromatic polycarbonate is reacted with an aliphatic polyol in the melt and in the presence of a catalyst.

BACKGROUND OF THE INVENTION

Polycarbonate molding compositions containing an aromatic carbonate polymer and an ester have been disclosed in GB 1,567,517. Accordingly, esters of certain organic acids and certain alcohols can be incorporated in a thermoplastic aromatic polycarbonate resulting in a resin having release properties. In addition, the composition is said to be compatible with polycarbonate melt. The incorporation of the esters in the polycarbonate composition in accordance with the '517 document can be effected by admixing the ester with granules of polycarbonate composition and subsequently extruding these through an extruder under standard conditions. The esters may also be incorporated by dissolving them in a solvent in which the polycarbonate is dissolved and subsequently recovering the polymer composition from the solvent by known methods.

The preparation of relevant copolycarbonates was disclosed by Schreckenberg in U.S. Pat. No. 4,281,101. The process involved solution reaction of oligomers with diphenols. In accordance with the process disclosed in the '101 document, an aliphatic aromatic polycarbonate with diphenol carbonate end groups is prepared by reacting in the melt an aliphatic diol, carbonic acid bis aryl ester—for example diphenyl carbonate—and diphenols. The resulting polycarbonate is characterized in that each of its end groups constitute a residue of one diphenol. The polycarbonate disclosed in the '101 document are unsuitable in the practice of the present invention for the preparation of block copolycarbonates. It was surprisingly found that in instances where each of the end groups constitute residues of less than 2 diphenol units, the oligocarbonate was unsuitable for the preparation of copolycarbonates by melt blending with a polycarbonate resin. The product made with such unsuitable oligocarbonate was typically delaminated.

DETAILED DESCRIPTION OF THE INVENTION

A process for preparing a block oligocarbonate is disclosed. The oligocarbonate conforms to

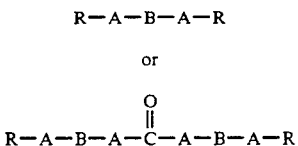

where R denotes hydrogen or

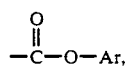

and where A denotes an aromatic carbonate structure conforming to

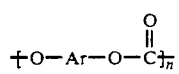

where Ar is an aromatic radical, n is 2-6 and where B is the residue of an aliphatic polyol, with the proviso that said B is bonded to said A through the terminal carboxyl in said A. The residue of an aliphatic polyol in the present context refers to that portion of the polyol remaining after the removal of the hydroxyl groups. The oligomeric block copolymer of the invention is useful as a reactant in the preparation of copolymers, preferably copolycarbonate resins having desirable properties.

In the practice of the invention there is produced an oligomeric block copolymer, herein block oligomer. The block oligomer may, in one embodiment of the invention, be end-capped upon a reaction with diphenyl carbonate. The block oligomer thus produced is useful for the preparation of copolymers. In the process of the invention, there is reacted in the melt, in the presence of a transesterification catalyst, an aromatic polycarbonate with an aliphatic polyol to produce to oligomer.

Aromatic polycarbonates within the scope of the present invention are homopolycarbonates and copolycarbonates and mixtures thereof.

The polycarbonates generally have a weight average molecular weight of 10,000-200,000, preferably 20,000-80,000 and their melt flow rate, per ASTM D-1238 at 300° C., is about 1 to about 65 gm/10 min., preferably about 2-15 gm/10 min. They may be prepared, for example, by the known diphasic interface process from a carbonic acid derivative such as phosgene and dihydroxy compounds by polycondensation (see German Offenlegungsschriften 2,063,050; 2,063,052; 1,570,703; 2,211,956; 2,211,957 and 2,248,817; French Patent 1,561,518; and the monograph H. Schnell, "Chemistry and Physics of Poly-carbonates", Interscience Publishers, New York, New York, 1964, all incorporated herein by reference).

In the present context, dihydroxy compounds suitable for the preparation of the polycarbonates of the invention include the compounds of structural formulae (1) or (2).

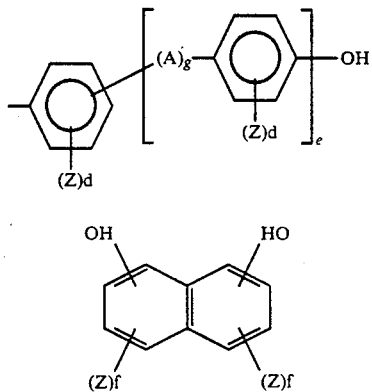

wherein

A denotes an alkylene group with 1 to 8 carbon atoms, an alkylidene group with 2 to 8 carbon atoms, a cycloalkylene group with 5 to 15 carbon atoms, a cycloalkylidene group with 5 to 15 carbon atoms, a carbonyl group, an oxygen atom, a sulfur atom, —SO—or—SO$_2$—or a radical conforming to

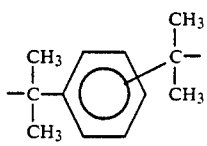

e and g both denote the number 0 to 1;

Z denotes F, Cl, Br or C$_1$–C$_4$-alkyl and if several Z radicals are substituents in one aryl radical, they may be identical or different from one another;

d denotes an integer of from 0 to 4; and f denotes an integer of from 0 to 3.

Among the dihydroxy compounds useful in the practice of the invention are hydroquinone, resorcinol, bis-(hydroxyphenyl)-alkanes, bis-(hydroxyphenyl)-ethers, bis-(hydroxyphenyl)-ketones, bis-(hydroxyphenyl)-sulfoxides, bis-(hydroxyphenyl)-sulfides, bis-(hydroxyphenyl)-sulfones, and α,α-bis-(hydroxyphenyl)-diisopropyl-benzenes, as well as their nuclear-alkylated compounds.

Also suitable are bisphenols which are derived from fluorenone

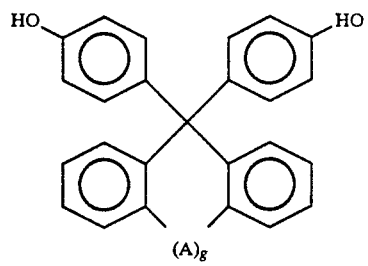

where A and g are described above.

These and further suitable aromatic dihydroxy compounds are described, for example, in U.S. Pat. No. 3,028,356; 2,999,835; 3,148,172; 2,991,273; 3,271,367; 4,982,014 and 2,999,846, all incorporated herein by reference.

Further examples of suitable bisphenols are 2,2-bis-(4-hydroxy-phenyl)-propane (bisphenol A), 2,4-bis-(4-hydroxyphenyl)-2-methyl-butane, 1,1-bis-(4-hydroxyphenyl)-cyclohexane, α,α'-bis-(4-hydroxyphenyl)-p-diisopropylbenzene, 2,2-bis-(3-methyl-4-hydroxyphenyl)-propane, 2,2-bis-(3-chloro-4-hydroxy phenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfide, bis-(3,5-dimethyl-4-hydroxyphenyl)-sulfoxide, bis-(3,5-dimethyl-4-hydroxyphenyl)-sulfone, dihydroxy-benzophenone, 2,4-bis-(3,5-dimethyl-4-hydroxy-phenyl)-cyclohexane, α,α'-bis-(3,5-dimethyl-4- hydroxyphenyl)-p-diisopropylbenzene and 4,4'-sulfonyl diphenol.

Examples of particularly preferred aromatic bisphenols are 2,2,-bis-(4-hydroxyphenyl)-propane, 2,2-bis-(3,5-dimethyl-4-hydroxyphenyl)-propane and 1,1-bis-(4-hydroxyphenyl)-cyclohexane.

The most preferred bisphenol is 2,2-bis-(4-hydroxyphenyl)-propane (bisphenol A).

The polycarbonates of the invention may entail in their structure units derived from one or more of the suitable bisphenols.

Among the resins suitable in the practice of the invention are included phenolphthalein-based polycarbonate, copolycarbonates and terpolycarbonates such as are described in U.S. Pat. Nos. 3,036,036 and 4,210,741, both incorporated by reference herein.

The polycarbonates of the invention may also be branched by condensing therein up to 5 mol percent, preferably 0.05-2.0 mol % (relative to the bisphenols) of polyhydroxyl compounds. Polycarbonates of this type have been described, for example, in German Offenlegungsschriften 1,570,533; 2,116,974 and 2,113,374; British Patents 885,442 and 1,079,821 and U.S. Pat. No. 3,544,514. The following are some examples of polyhydroxyl compounds which may be used for this purpose: phloroglucinol; 4,6-dimethyl-2,4,6-tri-(4-hydroxyphenyl)- heptane; 1,3,5-tri-(4-hydroxphenyl)-benzene; 1,1,1-tri-(4-hydroxyphenyl)-ethane; tri-(4-hydroxyphenyl)-phenylmethane; 2,2-bis-[4,4-(4,4'-dihydroxydiphenyl)]-cyclohexyl-propane; 2,4-bis-(4-hydroxy-l-isopropylidine)-phenol; 2,6-bis-(2'-dihydroxy-5'-methylbenzyl)-4-methylphenol; 2,4-dihydroxybenzoic acid; 2-(4-hydroxyphenyl)-2-(2,4-dihydroxyphenyl)-propane and 1,4-bis-(4,4'-dihydroxytriphenylmethyl)-benzene. Some of the other polyfunctional compounds are 2,4-dihydroxy-benzoic acid, trimesic acid, cyanuric chloride and 3,3-bis-(4-hydroxyphenyl)2-oxo-2,3-dihydroindole. In addition to the polycondensation process mentioned above, other processes for the preparation of the polycartonates of the invention are polycondensation in a homogeneous phase and transesterification. The suitable processes are disclosed in the incorporated herein by references, U.S. Pat. Nos. 3,028,365; 2,999,846; 3,153,008; and 2,991,273.

The preferred process for the preparation of polycarbonates is the interfacial polycondensation process.

Other methods of synthesis in forming the polycarbonates of the invention such as disclosed in U.S. Pat. No. 3,912,688, incorporated herein by reference, may be used.

Suitable polycarbonate resins are available in commerce, for instance, Makrolon FCR, Makrolon 2600, Makrolon 2800 and Makrolon CD2000, all of which are bisphenol based homopolycarbonate resins differing in terms of their respective molecular weights and characterized in that their melt flow indices (MFR) per ASTM D-1238 are about 16.5–24, 13–16, 7.5–13.0 and 50–60 gm/10 min., respectively. Also suitable are aromatic polyester carbonate and aromatic polyester resins available as APEC and APEC HT from Mobay and the widely known PBT and PET aromatic aliphatic polyester resins.

Suitable polycarbonate resins are known and methods of their preparation have been disclosed, for example in U.S. Pat. Nos. 3,030,331; 3,169,121; 3,395,119; 3,729,447; 4,255,556; 4,260,731; 4,369,303 and 4,714,746 all of which are incorporated by reference herein.

The aliphatic polyol in accordance with the present invention is an aliphatic compound having 1 or more hydroxyl functional groups and a molecular weight of up to 30,000. Included are polyester polyols and polyether polyols. Preferably the polyol has 2 to 5 hydroxyl groups, most preferably, the polyol is a diol.

Examples of the aliphatic polyors are aliphatic polyester polyols, aliphatic polyether polyols, aliphatic polyhydroxy polycarbonates, aliphatic polyhydroxy polyacetals, aliphatic silicone based polyols, aliphatic polyhydroxy polyacrylates, aliphatic polyhydroxy polyester amides and aliphatic polyhydroxy polythioethers. The aliphatic polyester polyols, aliphatic polyether polyols and aliphatic polyhydroxy polycarbonates are preferred.

Suitable aliphatic polyester polyols include reaction products of polyhydric, preferably dihydric alcohols to which trihydric alcohols may be added and polybasic, preferably dibasic carboxylic acids. Instead of these polycarboxylic acids, the corresponding carboxylic acid anhydrides or polycarboxylic acid esters of lower alcohols or mixtures thereof may be used for preparing the polyesters. The polycarboxylic acids may be aliphatic, cycloaliphatic or heterocyclic and they may be substituted, e.g. by halogen atoms, and/or unsaturated. The following are mentioned as examples: succinic acid; adipic acid; suberic acid; azelaic acid; sebacic acid; glutaric acid anhydride; maleic acid; maleic acid anhydride; fumaric acid; dimeric and trimeric fatty acids such as oleic acid, which may be mixed with monomeric fatty acids. Suitable polyhydric alcohols include, e.g. ethylene glycol; propylene glycol-(1,2) and -(1,3); butylene glycol-(1,4) and -(1,3); hexanediol-(1,6); octanediol-(1,8); neopentyl glycol; cyclohexanedimethanol (1,4-bis-hydroxymethylcyclohexane); 2-methyl-1,3-propanediol; 2,2,4-trimethyl1,3-pentanediol; triethylene glycol; tetraethylene glycol; polyethylene glycol; dipropylene glycol; polypropylene glycol; dibutylene glycol and polybutylene glycol, glycerine, sorbitol and trimethlyolpropane.

Also suitable are copolymers and cooligomers of ethylene and propylene glycols, pentaerythritol, mannitol, glucose, fructose, sucrose, affinoses, thioglycerol, thiodiglycol, thiomonoglycol and the like.

Aliphatic polycarbonates containing hydroxyl groups include those known per se such as the products obtained from the reaction of diols such as propanediol-(1,3), butanediol-(1,4) and/or hexanediol-(1,6), diethylene glycol, triethylene glycol or tetraethylene glycol with phosgene, or with cyclic carbonates such as ethylene or propylene carbonate. Also suitable are polyester carbonates obtained from the above-mentioned polyesters with phosgene, or cyclic carbonates.

Suitable aliphatic polyether polyors are obtained in known manner by the reaction of starting compounds which contain reactive hydrogen atoms with alkylene oxides such as ethylene oxide, propylene oxide, butylene oxide, tetrahydrofuran, epichlorohydrin or mixtures of these alkylene oxides. Suitable starting compounds containing reactive hydrogen atoms include the polyhydric alcohols set forth for preparing the polyester polyols and, in addition, water, methanol, ethanol, 1,2,6-hexane triol.

Polyethers modified by vinyl polymers are also suitable for the process according to the invention.

Suitable aliphatic polyhydroxy polyester amides and polyamines include the predominantly linear condensates obtained from polybasic saturated and unsaturated carboxylic acids or their anhydrides and polyvalent saturated or unsaturated aminoalcohols, diamines, polyamines and mixtures thereof.

Suitable monomers for producing hydroxy-functional polyacrylates include acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate and 2-isocyanatoethyl methacrylate.

The most preferred embodiment entails polyors having a molecular weight of up to 10,000 g/mole. The most preferred polyols in the present context are polyethylene glycol, polypropylene glycol and polyester polyol derived from a dimeric fatty acid and neopentyl glycol, having a molecular weight of about 2000 to 10,000 g/mole.

The catalysts suitable in the reaction are transesterification catalysts which are well known in the art. These include transition metal compounds, such as titanic and tetraalkyl esters, dialkyl-tin dicarboxylates, tin dicarboxylates, chelates of Fe, Zn, Co, Ni or Pb and carboxylates of Pb, Co, Ni or Fe, and bases such as tertiary amines or oxides, hydroxides, carbonates, alcoholates. phenolates or carboxylates of alkali metals or alkaline earth metals, imidizoles and pyridine derivatives, especially dimethyl amino pyridine. The catalyst is used in amounts of between 0.0001 and 1%, preferably 0.001 to 0.1% relative to the weight of the reaction mixture.

In the presence of a catalyst, the aliphatic hydroxyl performs a displacement of a phenol from a carbonate bond following the schematic

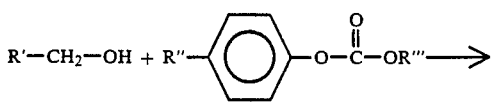

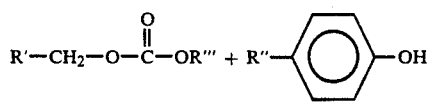

The reaction is known and is kinetically driven to favor displacement of phenolic groups. The result is "capping" of all the aliphatic hydroxyls with aromatic carbonate residues. The statistical chain length of the aromatic carbonate residues is determined by the ratio of the carbonate repeat units to aliphatic hydroxyls in the melt reaction. In the process of the invention it is critical that the chain length be at least 2, preferably at least 3, most preferably 3 to 4.

In the process for the preparation of the block oligomer of the invention the reaction proceeds at 180°–230° C., preferably 210°–225° C. while stirring until a homogeneous melt is obtained. Typically this may take about 1 to 3 hours. The resulting product conforms structurally to

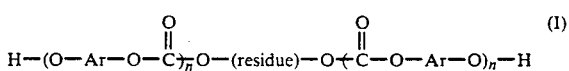

wherein "residue" denotes the residue of an aliphatic polyol as described above, Ar is an aromatic radical and n denotes the ratio of the carbonate repeat units to the aliphatic hydroxyls in the melt reaction. In an additional embodiment of the invention, in instances where it is desirable to have multiblock structures having higher molecular weight or if end-capping is desired, the resulting product (I) is reacted with diphenyl carbonate, phenol being distilled off. Typically, the amount of diphenyl carbonate used is 0.5 to 1 molar equivalents based on the hydroxy functionality. Use of less than a 1:1 ratio results in the build up of

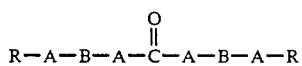

type of structures.

In the first instance, where a stoichiometric amount of diphenyl carbonate is reacted with the compound termed (I) above, the resulting product conforms to

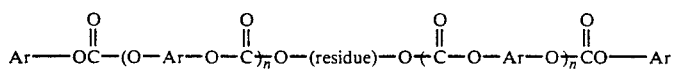

where the terms are as noted above.

In instances where the added phenyl carbonate is added in substoichiometric amounts, the resulting product conforms to

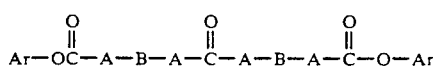

where A denotes

and where B denotes —O—(residue)—O—

Experimental: production of block oligomers

Block oligomers in accordance with the invention were prepared as follows:

Series 1. The A units were bisphenol-A oligocarbonate wherein n=1.5–3, and where the B units corresponded to

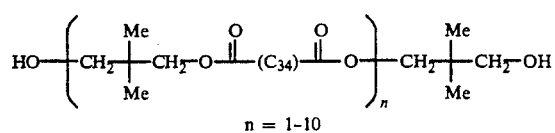

having a molecular weight of approximately 1000, 2000, 3000 and 4000 g/mol, n being about 1,3,5 and 6.

Series 2. Where A was a bisphenol-A oligocarbonate, n=3 and B corresponded to structure II

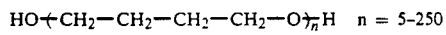

having a molecular weight of about 2000 g/mol

Series 3. A=BPA oligocarbonate, n=3; B corresponding to structure III

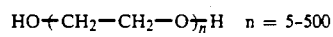

having a molecular weight of about 2000, 3400 and 8000 g/mol.

Series 4. A=BPA oligocarbonate, n=3; B corresponding to structure IV

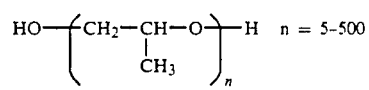

n=5–500 having a molecular weight of approximately 2000 and 4000 g/mol.

In the preparation of the blocks described above, the polymeric diol was heated under nitrogen atmosphere to about 180°–230° C. with stirring in a sturdy reactor. A polycarbonate resin (Makrolon homopolycarbonate) was added while stirring and while the temperature was maintained. Before completing the addition of the BPA polycarbonate there was added to the reactor a BPA-disodium salt catalyst. The reaction continued for about 1 to 3 hours while stirring. The resulting oligomers conformed structurally to

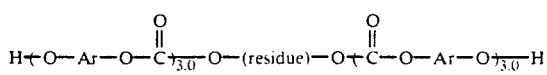

where the residue is derived from the polyether polyol or the polyester polyol as the case may be. The resulting products are suitable for reactive blending with polycarbonates.

In some applications, as was described above the capping with diphenyl carbonate is required where heat might cause unwanted degradation of polycarbonate caused by phenolic OH termination.

If and when the phenolic end groups are detrimental, they may in accordance with the present invention be further reacted with diphenyl carbonate. Accordingly, a stoichiometric equivalence of diphenyl carbonate based on the the starting aliphatic hydroxyl was added while stirring, at a temperature of about 20°-60° C. under nitrogen atmosphere. Vacuum was then slowly applied (1 Torr) to start removing phenol. Stirring continued until the evolution of phenol stopped.

The block oligomer of the present invention is suitable as a reactant for the preparation of copolymers.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a block oligocarbonate selected from the group consisting of

R—A—B—A—R and

R—A—B—A—C(=O)—A—B—A—R where R denotes

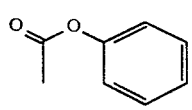

and where A denotes an aromatic carbonate structure conforming to

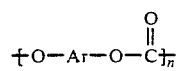

where n is 2-6, B is the residue of an aliphatic polyol, with the proviso that said B is bonded to said A through the terminal carboxyl in said A, and where Ar denotes an aromatic radical derived from the group consisting of

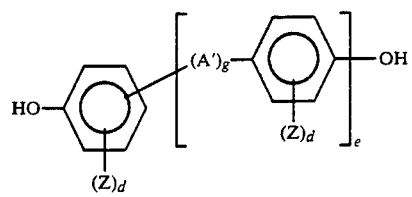

and

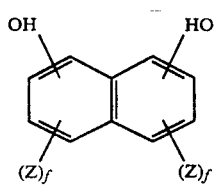

where A' denotes an $C_{1-8}$ alkylene group, $C_{2-8}$ alkylidene group, $C_{5-15}$ cycloalkylene group, $C_{5-15}$ cycloalkylidene group, carbonyl group, an oxygen atom, a sulfur atom, -SO-, -SO$_2$- or a radical conforming to

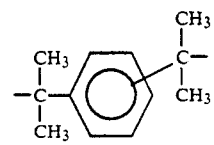

e and g denote 0 or 1, Z independently denotes F, Cl, Br or $C_{1-4}$-alkyl, d is an integer of 0 to 4 and f is an integer of 0 to 3, comprising
 a) reacting an aromatic polycarbonate with an aliphatic polyol and
 b) reacting the product of said a) with diphenyl carbonate,
characterized in that said a) is carried out in the melt at a temperature of 180°-230° C. in the presence of a transesterification catalyst and said polycarbonate having a weight average molecular weight of about 10,000 to 20,000, and where said aliphatic polyol has a molecular weight of up to about 30,000 and a functionality of 1 to 6.

2. The process of claim 1 wherein diphenyl carbonate is reacted at a stoichiometrically equivalent amount.

3. The process of claim 1 wherein diphenyl carbonate is reacted at less than a stoichiometrically equivalent amount.

4. The oligocarbonate produced by the process of claim 1.

5. The oligocarbonate produced by the process of claim 2.

6. The oligocarbonate produced by the process of claim 3.

7. The process of claim 1 wherein aliphatic polyol is polyether polyol.

8. The process of claim 1 wherein said aliphatic polyol has a molecular weight of about 1500 to 4000.

9. The process of claim 1 wherein said aliphatic polyol has a molecular weight of about 6000 to 10,000.

10. The block oligomer produced by the process of claim 7.

11. The block oligomer produced by the process of claim 8.

12. The block oligomer produced by the process of claim 9.

* * * * *